US00PP17782P2

(12) United States Plant Patent
Hooijman

(10) Patent No.: US PP17,782 P2
(45) Date of Patent: Jun. 5, 2007

(54) ***LIMONIUM* PLANT NAMED 'ESM ARA'**

(50) Latin Name: *Limonium sinuatum*
Varietal Denomination: Esm Ara

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 11/264,770

(22) Filed: Nov. 1, 2005

(51) Int. Cl.
*A01H 5/00* (2006.01)

(52) U.S. Cl. ..... Plt./358

(58) Field of Classification Search ..... Plt./358
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Limonium* plant named 'Esm Ara', characterized by its upright and somewhat outwardly spreading plant habit; long and strong flowering stems; vigorous and freely branching growth habit; freely and uniformly flowering habit; dense panicles with purple-colored flowers; and good postproduction longevity.

1 Drawing Sheet

Botanical designation: *Limonium sinuatum* cultivar Esm Ara.

BACKGROUND OF THE INVENTION

The present Invention relates to a new and distinct cultivar of *Limonium* plant, botanically known as *Limonium sinuatum,* and hereinafter referred to by the cultivar name Esm Ara.

The new *Limonium* is a product of a planned breeding program conducted by the Inventor in El Quinche, Pichincha, Ecuador. The objective of the breeding program was to create new freely branching *Limonium* cultivars with compact inflorescences and purple-colored flowers.

The new *Limonium* originated from a cross-pollination made by the Inventor in August, 2001 in El Quinche, Pichincha, Ecuador of a proprietary selection of *Limonium sinuatum* identified as Code 136, not patented, as the female, or seed, parent and an unidentified selection of *Limonium sinuatum,* not patented, as the male, or pollen, parent. The new *Limonium* was discovered and selected by the Inventor as a flowering plant within the progeny of the stated cross-pollination in a controlled environment in El Quinche, Pichincha, Ecuador.

Asexual reproduction of the new cultivar by terminal cuttings in El Quinche, Pichincha, Ecuador since February, 2002, has shown that the unique features of this new *Limonium* are stable and reproduced true to type in successive generations.

SUMMARY OF THE INVENTION

Plants of the cultivar Esm Ara have not been observed under all possible environmental conditions. The phenotype may vary somewhat with variations in environment such as temperature and light intensity without, however, any variance in genotype.

The following traits have been repeatedly observed and are determined to be the unique characteristics of 'Esm Ara'.

These characteristics in combination distinguish 'Esm Ara' as a new and distinct cultivar:

1. Upright and somewhat outwardly spreading plant habit.
2. Long and strong flowering stems.
3. Vigorous and freely branching growth habit.
4. Freely and uniformly flowering habit.
5. Dense panicles with purple-colored flowers.
6. Good postproduction longevity.

Plants of the new *Limonium* differ from plants of the female parent selection in the following characteristics:

1. Plants of the new *Limonium* have more durable leaves than plants of the female parent selection.
2. Plants of the new *Limonium* flower have denser inflorescences than plants of the female parent selection.
3. Plants of the new *Limonium* and the female parent selection differ in flower coloration as plants of the female parent selection have blue and white bi-colored flowers.

Plants of the new *Limonium* can be compared to the *Limonium* cultivar Crystal Dark Blue, not patented. In side-by-side comparisons conducted in El Quinche, Pichincha, Ecuador, plants of the new *Limonium* differed from plants of the cultivar Crystal Dark Blue in the following characteristics:

1. Plants of the new *Limonium* were narrower than plants of the cultivar Crystal Dark Blue.
2. Plants of the new *Limonium* had shorter internodes than plants of the cultivar Crystal Dark Blue.
3. Plants of the new *Limonium* had larger and more durable leaves than plants of the cultivar Crystal Dark Blue.
4. Plants of the new *Limonium* had many flowers per inflorescence than plants of the cultivar Crystal Dark Blue.
5. Plants of the new *Limonium* and the cultivar Crystal Dark Blue differed in flower color as plants of the cultivar Crystal Dark Blue have violet-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Limonium.*

The photographs at the top of the sheet comprises a side perspective view of typical flowering stems of 'Esm Ara'.

The photograph at the bottom of the sheet is a close-up view of a typical inflorescence of 'Esm Ara'.

DETAILED BOTANICAL DESCRIPTION

The aforementioned photographs, following observations and measurements describe plants grown in El Quinche, Pichincha, Ecuador, in a polyethylene-covered greenhouse and under commercial production practices. Plants were about eight months old when the photographs and description were taken. During the production of the plants, day temperatures ranged from 12° C. to 30° C., night temperatures ranged from 5° C. to 11° C. and light levels ranged from 1,000 foot candles to 1,150 foot candles. Plants were pinched about nine weeks after planting. In the following description, color references are made to The Royal Horticultural Society Colour Chart, 2001 Edition, except where general terms of ordinary dictionary significance are used.

Botanical classification: *Limonium sinuatum* cultivar Esm Ara.

Parentage:

*Female parent.*—Proprietary selection of *Limonium sinuatum* identified as Code 136, not patented.

*Male parent.*—Unidentified selection of *Limonium sinuatum,* not patented.

Propagation:

*Type cutting.*—Terminal vegetative cuttings.

*Time to initiate roots.*—About 20 days at 30° C. to 35° C.

*Time to produce a rooted young plant.*—About 35 to 42 days at 25° C. to 30° C.

*Root description.*—Fine, fibrous; 165A in color.

*Rooting habit.*—Moderately dense.

Plant description:

*Plant form/habit.*—Upright and somewhat outwardly spreading biennial typically used as a cut flower; erect inverted triangle; vigorous and freely branching growth habit; long and strong flowering stems with dense panicles.

*Plant height.*—About 105 cm.

*Plant width* (*spread*).—About 71.3 cm.

*Quantity of flowering stems produced per year.*—About 48.

*Lateral branches.*—Form: Angular, winged. Length: About 99 cm. Internode length: About 5.8 cm. Strength: Strong. Texture: Pubescent; rugose. Color: 137C.

*Foliage description.*—Arrangement: Alternate, simple; sessile. Length: About 34.8 cm. Width: About 7.6 cm. Shape: Lanceolate; dissected, sinuate. Apex: Acute. Base: Sheathed. Margin: Sinuate. Durability: Durable. Texture, upper and lower surfaces: Lamina, glabrescent; margins, pubescent, ciliate. Venation pattern: Pinnate. Color: Developing leaves, upper surface: 137C. Developing leaves, lower surface: 137B. Fully expanded leaves, upper surface: 137A to 147A. Fully expanded leaves, lower surface: 137B. Venation, upper surface: 148D. Venation, lower surface: 146D.

Flower description:

*Flower type/habit.*—Single, rotate and cupped flowers arranged in terminal panicles; flowers sessile; flowers face upright and outward. Panicles dense and flat-topped. Uniformly and freely flowering habit; about 1,423 flowers per inflorescence. Flowers not fragrant. Corolla not persistent; calyx persistent.

*Natural flowering season.*—Continuously flowering year round in Ecuador.

*Postproduction longevity.*—Individual flowers last about one to two days and flowering stems last about two weeks as a cut flower.

*Flower buds.*—Height: About 7.5 mm. Diameter: About 1.5 mm. Shape: Ellipsoidal. Color: Towards the base, 145D; towards the apex, 77B.

*Flowers.*—Diameter: About 6 mm. Depth: About 1.6 cm.

*Petals.*—Quantity per flower: Typically five in a single whorl. Length: About 1.4 cm. Width: About 3 mm. Shape: Deltoid. Apex: Cordate. Margin: Entire. Texture, upper and lower surfaces: Smooth, glabrous; membranous. Color: Developing and fully expanded petals, upper surface: Close to 155D. Developing and fully expanded petals, lower surface: Close to 155D.

*Sepals.*—Quantity per flower: Typically five fused; calyx, salverform. Calyx length: About 1.4 cm. Calyx diameter: About 7.3 mm. Apex: Obtuse. Texture, upper and lower surfaces: Smooth, glabrous. Color: Developing and fully developed sepals, upper surface: Towards the base, 144D; towards the apex, N82A. Developing and fully developed sepals, lower surface: Towards the base, 144D; towards the apex, N82A.

*Peduncles.*—Length: About 40 cm. Diameter with wings: About 20.5 mm. Diameter without wings: About 7.7 mm. Orientation: Erect to about 53° from vertical. Strength: Strong. Color: 137C.

*Reproductive organs.*—Stamens: Quantity per flower: Typically five. Anther shape: Round. Anther length: About 1.3 mm. Anther color: 1B. Pollen amount: Abundant. Pollen color: 1B. Pistils: Quantity per flower: Typically one. Pistil length: About 1.1 cm. Stigma shape: Filiform. Stigma color: Close to 155D. Style length: About 9.2 mm. Style color: Close to 155D. Ovary color: N144D.

*Fruits.*—Type: Indehiscent capsule. Length: About 5.2 mm. Diameter: About 1.6 mm. Texture: Smooth. Color: 177B to 200A.

*Seeds.*—Length: About 5.2 mm. Diameter: About 1.6 mm. Color: 177B to 200A.

Disease/pest resistance: Plants of the new *Limonium* have not been noted to be resistant to pathogens and pests common to *Limonium.*

High temperature tolerance: Plants of the new *Limonium* have been observed to tolerate temperatures up to about 40° C.

It is claimed:

1. A new and distinct cultivar of *Limonium* plant named 'Esm Ara', as illustrated and described.

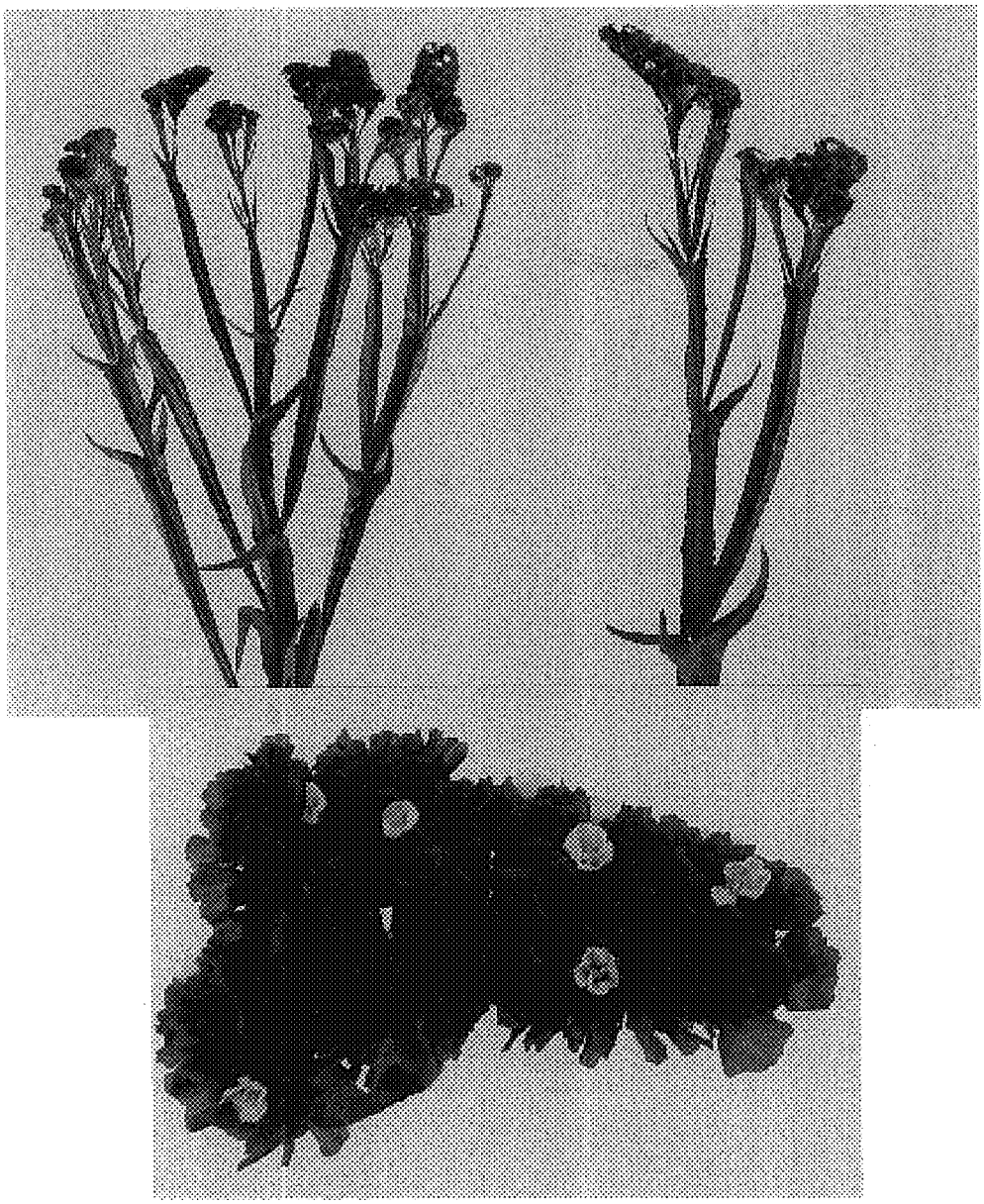

* * * * *